US008512968B2

(12) United States Patent
Van Lune

(10) Patent No.: US 8,512,968 B2
(45) Date of Patent: Aug. 20, 2013

(54) METHODS, REAGENTS AND KITS FOR LUCIFERASE ASSAY

(75) Inventor: Harry Van Lune, Aduard (NL)

(73) Assignee: Perkinelmer Health Sciences B.V., Groningen (NL)

( * ) Notice: Subject to any disclaimer, the term of this patent is extended or adjusted under 35 U.S.C. 154(b) by 417 days.

(21) Appl. No.: 12/739,691

(22) PCT Filed: Oct. 29, 2008

(86) PCT No.: PCT/NL2008/050676
§ 371 (c)(1),
(2), (4) Date: Feb. 9, 2011

(87) PCT Pub. No.: WO2009/058007
PCT Pub. Date: May 7, 2009

(65) Prior Publication Data
US 2011/0256564 A1    Oct. 20, 2011

Related U.S. Application Data

(60) Provisional application No. 60/983,443, filed on Oct. 29, 2007.

(30) Foreign Application Priority Data

Dec. 27, 2007   (EP) .................................... 07150428

(51) Int. Cl.
*C12Q 1/66*      (2006.01)
(52) U.S. Cl.
USPC .............................................. 435/8; 436/124
(58) Field of Classification Search
USPC ............................................ 435/8; 436/124
See application file for complete search history.

(56) References Cited

U.S. PATENT DOCUMENTS
2004/0219622 A1* 11/2004 Savage ............................... 435/8

FOREIGN PATENT DOCUMENTS
WO   WO-96/40988   12/1996
WO   WO-01/96862   12/2001

OTHER PUBLICATIONS

Goodwin, "Use of *Renilla* bioluminescence to illustrate nervous function," pp. 217-226 (2006), in Tested Studies for Laboratory Teaching, vol. 28 (M.A. O'Donnell, Editor), 2007. Proceedings of the 28th Workshop/Conference of the Association for Biology Laboratory Education (ABLE), 403 pages.*
Hori et al., "Structure of native *Renilla reniformis* luciferin," Proceedings of the National Academy of Sciences 74(10):4285-4287, 1977.*
Huang et al., "Effects of iodide on the fluorescence and activity of the hydroperoxyflavin intermediate of *Vibrio harveyi* luciferase," Photochemistry and Photobiology 81(2):435-430, 2005.*
International Search Report for PCT/NL2008/050676, mailed on Apr. 28, 2009, 2 pages.

* cited by examiner

*Primary Examiner* — Rosanne Kosson
(74) *Attorney, Agent, or Firm* — Morrison & Foerster LLP

(57) ABSTRACT

The invention relates to methods, reagents and kits for detecting enzyme activity using bioluminescence. In particular, it relates to a novel luciferase assay system with reduced background luminescence to allow for increased detection sensitivity. Provided is a method of detecting luciferase activity in a sample using coelenterazine or an analog thereof as a substrate, comprising: (a) initiating luciferase-catalyzed luminescence production by contacting said sample with a luciferase detection reagent to yield a reaction mixture, said reagent comprising coelenterazine and at least one iodide source in an amount sufficient to reduce the autoluminescence of said coelenterazine, (b) incubating said reagent mixture under conditions suitable to produce luminescence, and (c) measuring the luminescence produced. Also provided are detections reagents and kits for use in such a method.

8 Claims, 3 Drawing Sheets

METHODS, REAGENTS AND KITS FOR LUCIFERASE ASSAY

CROSS-REFERENCE TO RELATED APPLICATIONS

Figure 1:
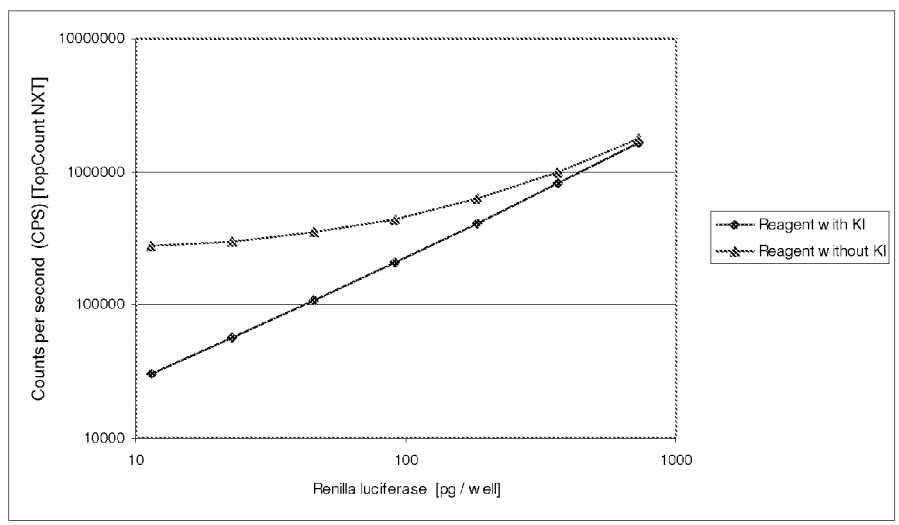

This application is the national phase of PCT application PCT/NL2008/050676 having an international filing date of 29 Oct. 2008, which claims benefit of US provisional application No. 60/983,443 filed 29 Oct. 2007, and European application No. 07150428.6 filed 27 Dec. 2007. The contents of the above patent applications are incorporated by reference herein in their entirety.

The invention relates to methods, reagents and kits for detecting enzyme activity using bioluminescence. In particular, it relates to a novel luciferase assay system with reduced background luminescence to allow for increased detection sensitivity.

BACKGROUND OF THE INVENTION

Luciferases are enzymes commonly used as reporters when analyzing molecular events in cells. When used as a reporter, the amount of luciferase in a cell can be indicative of a particular cellular event or condition. As such, many assays have been developed for measuring the amount of luciferase contained in biological samples. These assays typically involve assessing the amount of luciferase present in the sample by measuring the amount of luciferase enzymatic activity, and luciferase enzymatic activity is reflected by the destruction of luciferase enzymatic substrate or creation of a corresponding reaction product. Luciferases can react with a suitable substrate to produce light as one of the reaction products. The amount of light of this luminescent reaction can be measured, and used to determine the presence or amount of luciferase in a sample.

Luciferases that use coelenterazine as a substrate to produce luminescence include Renilla, Gaussia, Metridia and Obelia. These luciferases catalyse the oxidation of coelenterazine to yield coelenteramide, $CO_2$ and light. This reaction is shown below:

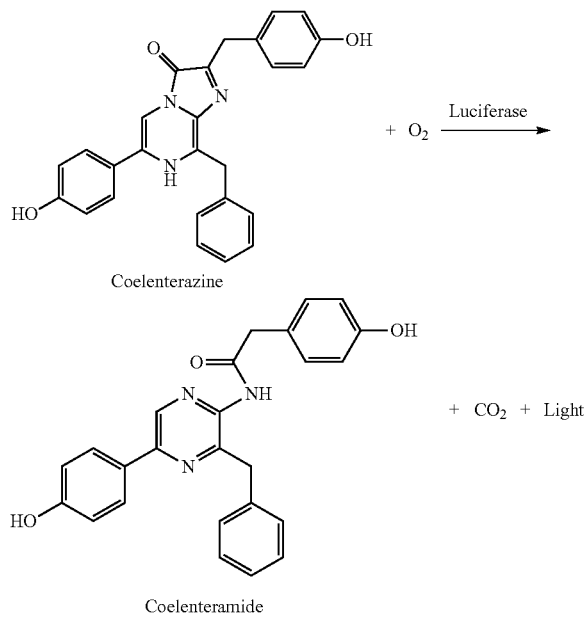

It is well known that coelenterazine can be oxidized and produce light in the absence of luciferase. Luminescence produced in this way is called autoluminescence. This autoluminescence creates a background signal and thus reduces the sensitivity of luciferase detection assays. In particular, coelenterazine autoluminescence reduces the ability to detect small amount of luciferase, such as when the autoluminescence signal is of similar magnitude to the luminescent signal generated by the luciferase.

Unwanted coelenterazine autoluminescence may be increased by certain assay components, including components of the sample to be tested and desired assay components, such as detergents and proteins. Non-ionic detergents, for example, are often used as cell lysis agents to solubilize luciferase and make substrate accessible, while proteins are typically present in samples to be tested (e.g. cells, cell culture media supplemented with serum). Thus, under many desirable assay conditions, autoluminescence of coelenterazine can reduce sensitivity of luciferase assays.

SUMMARY OF THE INVENTION

The present invention therefore aims to reduce such unwanted coelenterazine autoluminescence, thereby increasing the sensitivity of the luciferase detection assay and allowing lower amounts of luciferase to be detected. As is described herein, conditions for reducing autoluminescence of coelenterazine, and analogs thereof, have been identified. Specifically, it has been observed that addition of iodide to a luciferase reaction mixture can significantly reduce coelenterazine autoluminescence.

Accordingly, the invention relates to a method of detecting luciferase activity in a sample using coelenterazine or an analog thereof as a substrate, comprising: (a) initiating luciferase-catalyzed luminescence production by contacting said sample with a luciferase detection reagent to yield a reaction mixture, said reagent comprising coelenterazine and at least one iodide source in an amount sufficient to reduce the autoluminescence of said coelenterazine, (b) incubating said reagent mixture under conditions suitable to produce luminescence and (c) measuring the luminescence produced.

As used herein, the term "iodide source" refers to any compound capable of providing iodide ions in an aqueous solution. An iodide ion is an iodine atom with a −1 charge. Compounds with iodine in formal oxidation state −1 are thus called iodides. These include ionic compounds such as iodide salts. In view of the required compatibility with the assay conditions, the use of an iodide source which is soluble under aqueous conditions is of course preferred. Most ionic iodides are soluble, with the exception of yellow silver iodide and yellow lead iodide. A chemical test for an iodide compound is to acidify the aqueous compound by adding some drops of acid, to dispel any carbonate ions present, then adding lead nitrate, yielding a bright yellow precipitate of lead iodide. The particular iodide source will be the choice of the user, and can be selected based on such factors as solubility, toxicity and availability of iodide salts. Exemplary iodide sources include iodide salts such as NaI, KI, LiI, $NH_4I$ and the like, and in any combination with each other. Also of use for practicing the present invention are iodine compounds that dissociate to some extent to yield free iodide in solution.

As is exemplified in the Examples below, autoluminescence of coelenterazine and its analogs is significantly reduced when a luciferase reaction mixture comprising coelenterazine also comprises at least one iodide source. The ability of iodide to reduce autoluminescence of coelenterazine and its analogs was observed to be independent of the type of luciferase tested, such that this effect was observed when testing Renilla and Gaussia luciferases. Moreover, iodide was effective for reducing autoluminescense of nine different coelenterazine analogs (Example 6). Therefore, in one embodiment the coelenterazine used in accordance with the present invention is selected from the group consisting of native coelenterazine and coelenterazine analogs, such as coelenterazine cp, coelenterazine f, coelenterazine fcp, coelenterazine h, coelenterazine hcp, coelenterazine i, coelenterazine ip and coelenterazine n. The coelenterazine or analog thereof may be used in a concentration normally used. In one embodiment, the coelenterazine or analog thereof is present in the reaction mixture in a concentration of 2-5 µM, preferably in the presence of a metal chelating agent, for example a 1-10 mM EDTA buffer solution having a pH between 7.2-8.0.

Luciferase reaction mixtures comprising an iodide source are known in the art. WO96/40988 relates to quenching reagents and assays for enzyme-mediated luminescence. It discloses a method for reducing "refractive cross talk" between different sample wells using a quenching reagent that is added to the reaction mixture following initiation and detection of luciferase-catalyzed luminescence production. In this way, unwanted cross-talk of the sample with surrounding samples wells in which the luciferase reaction has not yet been initiated is prevented. Disclosed is an experiment in which Renilla luciferase is allowed to react with coelenterazine, after which NaI is added as quenching reagent. Thus, in contrast to the present invention wherein a luciferase reaction is initiated by combining sample and substrate in the presence of an iodide source, in the prior art method the iodide added to the sample separately from the substrate after measurement of the luminescence produced. The iodide is absent during the initiation and incubation phase of the luciferase reaction. Accordingly, a detection reagent comprising coelenterazine and an iodide source but not luciferase enzyme is neither disclosed in the art. Good results of reducing the autoluminescence of coelenterazine according to a method of the present invention are obtained when iodide is present in the luciferase detection reagent or the final luciferase reaction mixture (for example, a sample mixed with luciferase detection reagent) in a concentration of about 0.02 mM to about 500 mM iodide. Exemplified herein below is the effectiveness of iodide concentrations of 0.25 mM (Examples 4 and 5); 0.5 mM (Example 6); 2.5 mM (Example 1); and 50 mM (Examples 2 and 3). Thus, in one embodiment of the invention, the initiation of the luciferase reaction with a luciferase detection reagent, comprising coelenterazine (analog) and at least one iodide source, is performed in the presence of about 0.02 mM to about 500 mM iodide, like 1 to 250 mM, or 10 to 100 mM. In a specific aspect, the luciferase reaction mixture contains 0.02 to 500 mM of an iodide salt, preferably KI.

Thus, the present invention discloses the use of an iodide compound as a novel and inventive component in a luciferase detection reagent. Typically, a detection reagent according to the invention does not comprise a luciferase since the enzyme will be provided (if present) in the sample to be tested. The invention therefore also provides a luciferase detection reagent comprising coelenterazine or an analog thereof in combination with an iodide source, wherein said reagent does not comprise a luciferase.

Other components are described in the exemplary reaction conditions provided herein. Generally, for detecting luciferase in a cell-containing sample, a luciferase detection reagent includes luciferase substrate, such as coelenterazine; a buffer system to maintain the pH (for example, Good's Buffers, phosphate, Tris based buffers, and the like); a non-ionic detergent (for example, Tergitol NP-9, Igepal CA-630, Thesit, Triton X100, and the like) to lyse the cells and/or to inhibit the luciferase activity (to increase the half-life of the luminescence). Additional useful components can include, for example, a metal chelating agent (for example EDTA) to prevent degradation of the luciferase by suppressing the activity of metal-dependent proteases; and a reducing agent (for example, sodium thiosulfate, TCEP, DTT and the like) to reduce degradation of the coelenterazine in the luciferase detection reagent. In one embodiment, there is provided a luciferase detection reagent comprising coelenterazine or an analog thereof in combination with an iodide source, and furthermore comprising a buffer system, non-ionic detergent, a metal chelating agent, and/or a reducing agent, wherein the reagent does not comprise a luciferase.

Still a further aspect relates to an assay kit for performing a method of the present invention. Said kit for detecting luciferase in a sample comprises a first container comprising a luciferase detection reagent according to the invention, a second container comprising another useful assay component such as a buffer reagent or a luciferase standard, and/or directions for using the kit. Each reagent may have its own container or several reagents may be pre-mixed and packaged together in a container. In one embodiment, the coelenterazine in the assay kit is selected from the group consisting of native coelenterazine and coelenterazine analogs, including coelenterazine cp, coelenterazine f, coelenterazine fcp, coelenterazine h, coelenterazine hcp, coelenterazine i, coelenterazine ip and coelenterazine n.

As will be clear from the above, various types of iodide compounds may be used to reduce the autoluminescence of coelenterazine. An exemplary assay kit comprises an iodide salt, preferably selected from the group consisting of NaI, KI, LiI, and $NH_4I$. Other useful kit components are known in the art. Through the use of iodide in combination with coelenterazine (analog), this assay kit yields reliable, linear results with minimal autoluminescence background and superior sensitivity.

Also provided is the use of an iodide source to reduce the autoluminescence of coelenterazine or an analog thereof, to improve the detection sensitivity in a bioluminescence assay system that employs coelenterazine or an analog thereof as a substrate. Said assay system is preferably a luciferase assay system. The surprising effect of iodide as disclosed herein may be of use in any in vitro, an in situ and/or in an in vivo situation wherein coelenterazine or an analog thereof is used as substrate.

LEGENDS TO THE FIGURES

FIG. 1: The presence of an iodide source (KI) in a luciferase assay mixture improves detection of Renilla luciferase activity. Different amounts of luciferase were assayed as described in Example 1.

Figure 2:
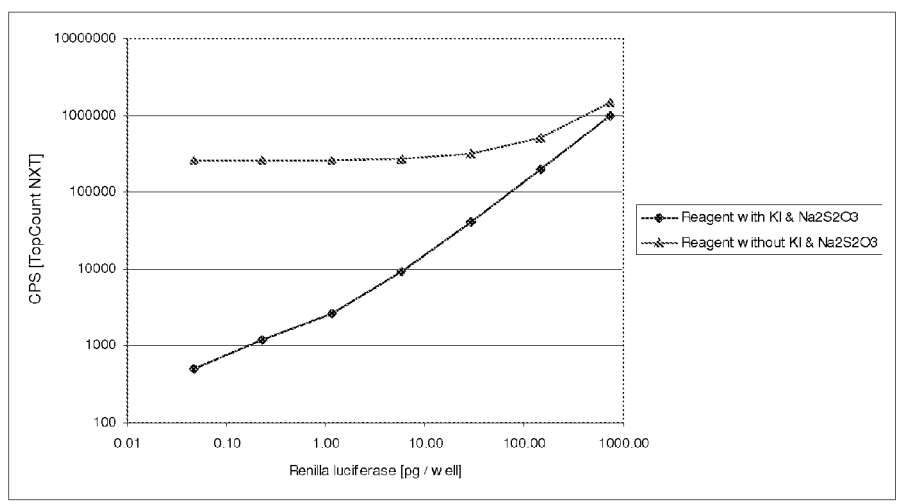

FIG. 2. Potassium iodide (KI) and sodium thiosulfate pentahydrate ($Na_2S_2O_3$) reduce coelenterazine autoluminescence, allowing for detection of less than 0.1 pg of luciferase. For details, see Example 2.

Figure 3:
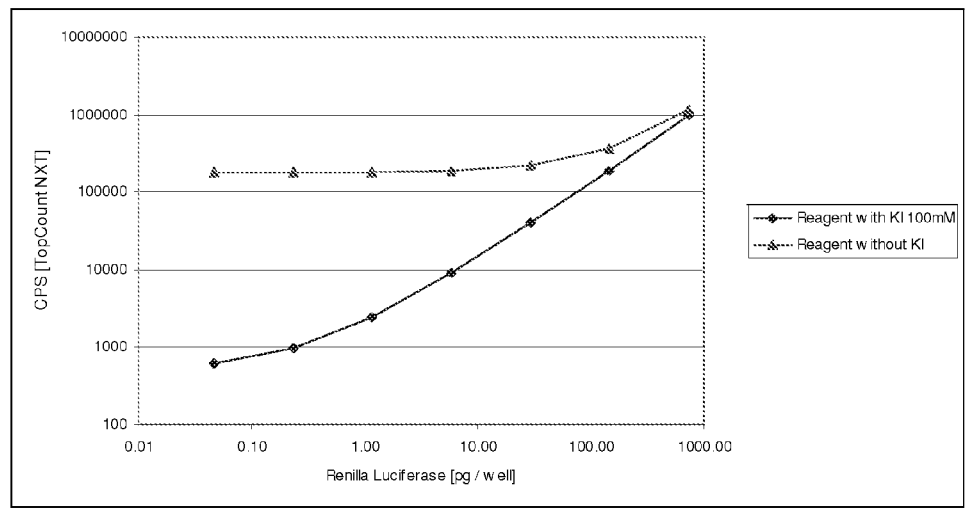

FIG. 3: Renilla luciferase activity was tested in the presence of absence of KI (see Example 4)

FIG. 4: Supernatants from CHO cells expressing Gaussia luciferase (positive) or CHO cells transfected with control vector (negative) were assayed in the presence (panel 4A) or absence (panel 4B) of an iodide source. For details, see Example 5.

Figure 5:
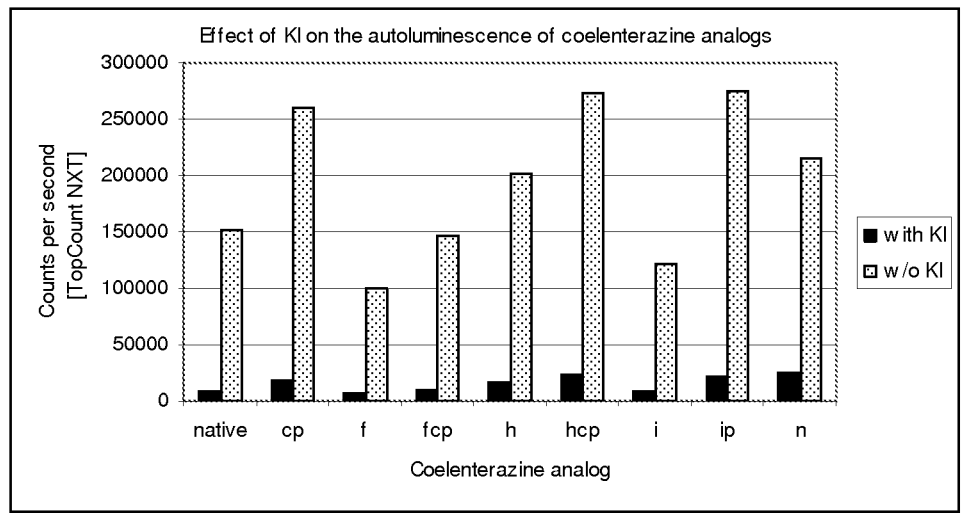

FIG. 5: The addition of iodide reduces the autoluminescence of both native coelenterazine as well as of coelenterazine analogs.

DETAILED DESCRIPTION OF THE INVENTION

EXPERIMENTAL SECTION

The Examples below describe luciferase assay compositions in which the sensitivity of luciferase detection was enhanced by reducing autoluminescence of the luciferase substrate coelenterazine. Although potassium iodide was used as an iodide source in the following Examples, it is noted that other iodide salts will yield substantially the same result.

Example 1

This example shows that the presence of an iodide source in a luciferase reagent mixture improves detection of Renilla luciferase activity.

Components of the tested luciferase detection reagent used to obtain an iodide-containing reaction mixture are shown in Table 1 below. A corresponding control luciferase detection reagent lacking an iodide source was prepared as a negative control.

TABLE 1

| Component | Vendor/Cat. no. | Concentration in detection reagent |
|---|---|---|
| HEPES | Sigma/H9136 | 25 mM |
| Tergitol NP-9 | Sigma/NP-9 | 0.5% |
| KI | Sigma/P8256 | 5 mM |
| Coelenterazine | Biosynth AG/C-7000 | 14 µM | pH adjusted to 7.0 with NaOH

In general, the coelenterazine was added from a stock solution of 1.4 mM coelenterazine in acidified ethanol. This stock solution was prepared as follows: to 1 mL of ethanol Absolute, 25 µL, of 2 M HCl was added. Coelenterazine (3 mg) was added to this solution and dissolved. Hereafter the solution was supplemented with 4 mL ethanol Absolute, resulting in the coelenterazine stock solution.

As luciferase sample a GST-fused Renilla luciferase from Chemicon (Cat. no: 4400) was used. Renilla luciferase was dissolved in 1 mL of Dulbecco's PBS/0.1% BSA to prepare a stock solution at 7.3 µg/mL. 10 µl of this stock solution was added to 10 mL of cell culture medium (DMEM without phenol red supplemented with 10% FBS, 2 mM L-Glutamine and 1 mM pyruvate, all from Invitrogen) resulting in a luciferase concentration of 7.3 ng/mL. This luciferase solution was serial diluted (1 over 2) to prepare a dilution series of Renilla luciferase in medium ranging from 7.3 ng/mL down to 110 pg/mL. The serial dilutions were added at 100 µL, per well to a CulturPlate-96 white (PerkinElmer Cat. no: 6005680) in triplicate for each luciferase detection solution. To these wells the luciferase detection reagent or control solution was added at 100 µL per well, to initiate the luminescence production. The resulting reaction mixtures were consequently incubated to allow for luciferase-catalyzed luminescence production. After shaking the plate briefly to mix the contents of the wells, the plate was loaded into a TopCount NXT Scintillation and Luminescence Counter (PerkinElmer) and luminescence measured after 5 minutes count delay.

In FIG. 1 the results of this experiment are shown. These results show that in the presence of 2.5 mM KI lower amounts of luciferase in the samples can be detected, as a result of the reduced coelenterazine autoluminescence.

Example 2

In essence, the same experiment was performed as in Example 1. Components of the tested luciferase detection reagent are shown in Table 2 below.

TABLE 2

| Component | Vendor/Cat. no. | Concentration in detection reagent |
|---|---|---|
| HEPES | Sigma/H9136 | 25 mM |
| Tergitol NP-9 | Sigma/NP-9 | 0.5% |
| KI | Sigma/P8256 | 100 mM |
| $Na_2S_2O_3 \cdot 5H_2O$ (sodium thiosulfate pentahydrate) | Sigma/S8503 | 10 mM |
| Coelenterazine | Biosynth AG/C-7000 | 14 µM | pH adjusted to 7.0 with NaOH

A corresponding control luciferase detection reagent, lacking both iodide and sodium thiosulfate pentahydrate, was also prepared.

In this experiment, Renilla luciferase was serial diluted (1 over 5) in cell culture medium (DMEM without phenol red supplemented with 10% FBS, 2 mM L-Glutamine and 1 mM pyruvate, all from Invitrogen).

As before, luciferase detection reagent or control solution was added at 100 µL per well, to initiate the luminescence production. The resulting reaction mixtures were consequently incubated to allow for luciferase-catalyzed luminescence production. After shaking the plate briefly to mix the contents of the wells, the plate was loaded into a TopCount NXT Scintillation and Luminescence Counter (PerkinElmer) and luminescence measured after 5 minutes count delay.

The results of this experiment are shown in FIG. 2. These results show significantly reduced coelenterazine autoluminescence in the presence of 50 mM KI and 5 mM sodium thiosulfate pentahydrate. Under these conditions, less than 0.1 pg per well of luciferase can be detected.

Example 3

In essence the same experiment was performed as in Example 1. Components of the tested luciferase detection reagent are shown in Table 3 below. A corresponding control luciferase detection reagent without iodide was also prepared.

TABLE 3

| Component | Vendor/Cat. no. | Concentration in detection reagent |
|---|---|---|
| HEPES | Sigma/H9136 | 50 mM |
| Tergitol NP-9 | Sigma/NP-9 | 0.5% |
| EDTA | Sigma/ED2SS | 5 mM |
| KI | Sigma/P8256 | 100 mM |
| $Na_2S_2O_3 \cdot 5H_2O$ | Sigma/S8503 | 10 mM |
| Coelenterazine | Biosynth AG/C-7000 | 21 µM | pH adjusted to 7.8 with NaOH

Renilla luciferase, serial diluted (1 over 5) in cell culture medium (see Example 2) was used as a sample in this experiment. The results (FIG. 3) show a significant reduction in coelenterazine autoluminescence in the presence of 50 mM KI. Under these conditions, less than 0.1 pg per well of luciferase can be detected.

Example 4

In this example a luciferase assay reagent is used for detecting Gaussia luciferase. Components of the tested luciferase detection reagent are shown in Table 4 below. Two corresponding control luciferase detection reagents were prepared: one lacking iodide, and one lacking potassium iodide and the reducing agent sodium thiosulfate pentahydrate ($Na_2S_2O_3 \cdot 5H_2O$).

TABLE 4

| Component | Vendor/Cat no. | Concentration in detection reagent |
|---|---|---|
| $Na_2HPO_4 \cdot 2H_2O$ | Merck/1.06580 | 100 mM |
| Citric Acid•$H_2O$ | Sigma/C1909 | 93 mM |
| Tergitol NP-9 | Sigma/NP-9 | 0.5% |
| KI | Sigma/P8256 | 0.5 mM |
| $Na_2S_2O_3 \cdot 5H_2O$ | Sigma/S8503 | 1 mM |
| Coelenterazine | Biosynth AG/C-7000 | 7 μM | pH 5.15

The coelenterazine was added from a 1.4 mM stock solution in acidified ethanol (see Example 1).

Gaussia Luciferase Samples Used:
  Supernatants (Gaussia luciferase is secreted from the cells) from CHO cells 24 hours post transfection (medium: MEM+Phenol Red supplemented with L-Glutamine and 5% FBS).
    Positive: CHO cells transfected with CMV-GLUC (6 μg of DNA)
    Negative: CHO cells transfected with Basic-GLUC (negative control)

These supernatants were diluted 100 times in medium (MEM+Phenol Red/5% FBS) resulting in the final Gaussia Luciferase Samples. (MEM: Invitrogen Cat no: 41090). The Positive, Negative Control Samples and plain medium as blank were added at 100 μL per well to a white CulturPlate-96.

To these wells the 3 different luciferase detection solutions were added at 100 μL per well, to initiate the luminescence production. The resulting reaction mixtures were consequently incubated to allow for luciferase-catalyzed luminescence production. After shaking the plate briefly to mix the contents of the wells, the plate was loaded into the TopCount NXT and luminescence measured after 15 minutes count delay.

The results of this experiment are shown in Table 5.

TABLE 5

| Detection Solution | Count per second CPS [TopCount NXT] | | |
|---|---|---|---|
| | Positive sample | Negative control | Blank (medium) |
| With KI & $Na_2S_2O_3$ | 510772 | 582 | 303 |
| Without KI With $Na_2S_2O_3$ | 455958 | 3864 | 3609 |
| Without KI and $Na_2S_2O_3$ | 446965 | 4225 | 4141 |

Clearly, the presence of an iodide source in the reaction mixture greatly reduces the background luminescence. This effect was much more pronounced than the effect of the reducing agent sodium thiosulfate.

Example 5

In this example a luciferase assay reagent is used for detecting Gaussia luciferase. Components of the tested luciferase detection reagent are shown in Table 6 below. A corresponding control luciferase detection reagent lacking iodide was also prepared.

TABLE 6

| Component | Vendor/Cat no. | Concentration in detection reagent |
|---|---|---|
| $Na_2HPO_4 \cdot 2H_2O$ | Merck/1.06580 | 100 mM |
| Citric Acid•$H_2O$ | Sigma/C1909 | 93 mM |
| Tergitol NP-9 | Sigma/NP-9 | 0.5% |
| KI | Sigma/P8256 | 0.5 mM |
| $Na_2S_2O_3 \cdot 5H_2O$ | Sigma/S8503 | 1 mM |
| Coelenterazine | Biosynth AG/C-7000 | 21 μM | pH 5.15

The Gaussia luciferase samples (Positive and Negative) were serial diluted (1 over 5) in MEM/5% FBS medium. These dilutions were added to the wells of a white 96-well CulturPlate at 100 μL per well. Subsequently, 100 μL of the different luciferase detection reagents was added to these wells, to initiate the luminescence production. The resulting reaction mixtures were consequently incubated to allow for luciferase-catalyzed luminescence production. After shaking the plate briefly, the plate was loaded into the TopCount NXT and luminescence was measured after 15 minutes count delay.

Figure 4A:
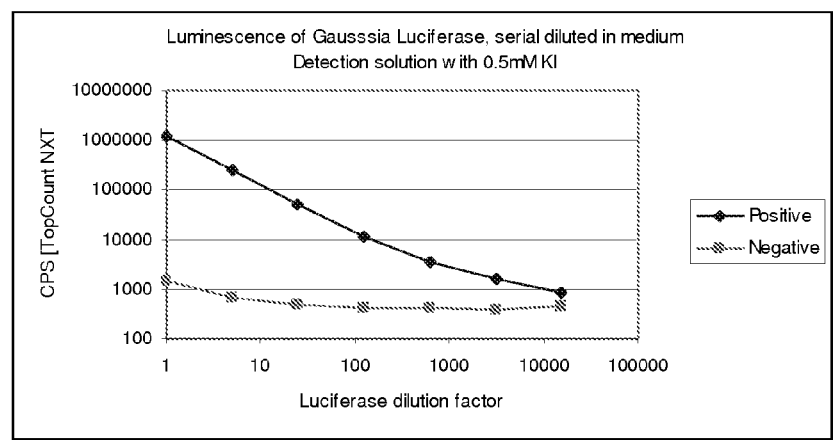
Figure 4B:
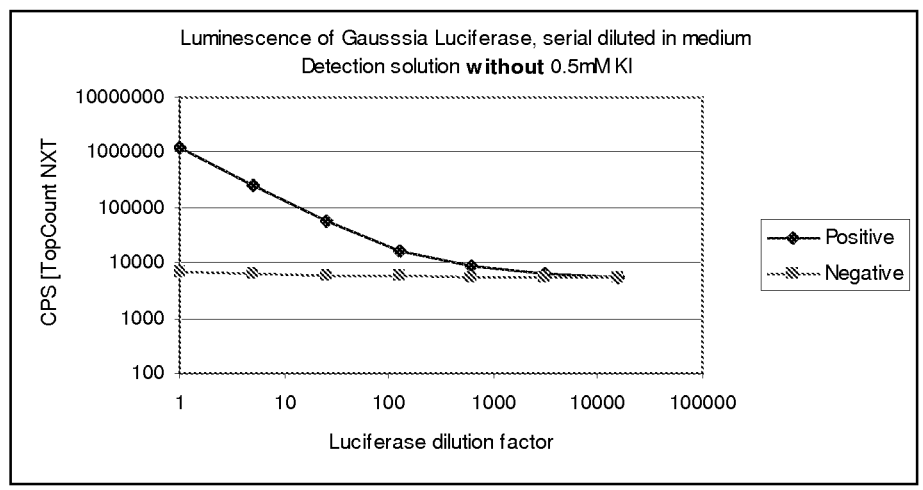

The results of the 2 different detection solutions are shown in FIGS. 4A and 4B. They demonstrate the improved sensitivity of detection in the presence of an iodide source.

Example 6

This example shows that the use of an iodide source is also useful for reducing autoluminescence of coelenterazine analogs.

The effect of iodide on the autoluminescence of nine different coelenterazine analogs was tested. Components of the tested luciferase detection reagent are shown in Table 7 below. A corresponding control luciferase detection reagent lacking an iodide source was also prepared.

TABLE 7

| Component | Vendor/Cat. no. | Concentration in detection reagent |
|---|---|---|
| HEPES | Sigma/H9136 | 50 mM |
| Tergitol NP-9 | Sigma/NP-9 | 0.5% |
| KI | Sigma/P8256 | 1 mM and 0 mM |
| $Na_2S_2O_3 \cdot 5H_2O$ (sodium thiosulfate pentahydrate) | Sigma/S8503 | 1 mM |
| Coelenterazine analogs | Biotium/10123 | 2.5 μg/mL | pH adjusted to 7.8 with NaOH

Coelenterazine Analogs Tested:
native coelenterazine, coelenterazine cp, coelenterazine f, coelenterazine fcp, coelenterazine h, coelenterazine hcp, coelenterazine i, coelenterazine ip and coelenterazine n.

The coelenterazine analogs were dissolved in ethanol at 25 μg/50 μL. To 1 mL of detection solution 5 μL of the coelenterazine stocks were added resulting in coelenterazine concentration of 2.5 μg/mL detection solution.

The detection solutions (with and without KI) with the 9 different coelenterazine analogs were tested. To the wells of a white 96-well CulturPlate, 100 μL Dulbecco's PBS (Invitrogen Cat. no.14040) supplemented with 0.1% BSA (Sigma A7030) was added. Subsequently, 100 μL of the detection solutions were added to these wells, to initiate the luminescence production. The resulting reaction mixtures were consequently incubated to allow for luciferase-catalyzed luminescence production. Next, the plate was briefly shaken to mix the contents of the wells. Hereafter the plate was loaded into the TopCount NXT and luminescence measured after 5 minutes count delay.

The results illustrated in FIG. 5 show that the addition of iodide reduces the autoluminescence of all coelenterazine analogs tested.

The invention claimed is:

1. A method of detecting luciferase activity in a sample using coelenterazine or an analog thereof as a substrate, comprising:
   a) preparing a reaction mixture by contacting said sample with coelenterazine or an analog thereof and with at least one iodide source in an amount sufficient to reduce the autoluminescence of said coelenterazine or analog,
   b) incubating said reaction mixture under conditions suitable to produce luminescence, and
   c) measuring the luminescence produced.

2. The method of claim 1, wherein said at least one iodide source is an iodide salt.

3. The method of claim 1, wherein the coelenterazine or analog is selected from the group consisting of native coelenterazine, coelenterazine cp, coelenterazine f, coelenterazine fcp, coelenterazine h, coelenterazine hcp, coelenterazine i, coelenterazine ip and coelenterazine n.

4. The method of claim 1, wherein the coelenterazine or analog thereof is present in the reaction mixture in a concentration of 2-5 µM.

5. The method of claim 1, wherein said reaction mixture comprises about 0.02 mM to about 500 mM iodide.

6. The method of claim 2 wherein said iodide salt is selected from the group consisting of NaI, KI, LiI and $NH_4I$, or any combination thereof.

7. The method of claim 1 wherein the reaction mixture is a 1-10 mM EDTA buffer solution having a pH between 7.2-8.0.

8. The method of claim 4 wherein the reaction mixture is a 1-10 mM EDTA buffer solution having a pH between 7.2-8.0.

* * * * *

UNITED STATES PATENT AND TRADEMARK OFFICE
CERTIFICATE OF CORRECTION

PATENT NO.        : 8,512,968 B2                                                                Page 1 of 1
APPLICATION NO.   : 12/739691
DATED             : August 20, 2013
INVENTOR(S)       : Harry Van Lune It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 702 days.

Signed and Sealed this

Fifteenth Day of September, 2015

Michelle K. Lee
*Director of the United States Patent and Trademark Office*